United States Patent [19]

Mackool

[11] Patent Number: 5,026,393
[45] Date of Patent: Jun. 25, 1991

[54] METHOD OF IMPLANTING AN INTRAOCULAR LENS IN A HUMAN EYE AND INTRAOCULAR LENS FOR SAME

[76] Inventor: Richard J. Mackool, 31-27 41st St., Astoria, N.Y. 11103

[21] Appl. No.: 145,906

[22] Filed: Jan. 20, 1988

[51] Int. Cl.$^5$ ............................................. A61F 2/16
[52] U.S. Cl. ........................................ 623/6; 606/107
[58] Field of Search ...................... 623/6; 128/303 R; 206/5.1; 606/1, 107

[56] References Cited

U.S. PATENT DOCUMENTS

| | | | |
|---|---|---|---|
| 4,373,218 | 2/1983 | Schachar | 623/6 |
| 4,585,457 | 4/1986 | Kalb | 623/6 |
| 4,681,102 | 7/1987 | Bartell | 128/303 R |
| 4,702,244 | 10/1987 | Mazzocco | 128/303 R |
| 4,715,373 | 12/1987 | Mazzocco et al. | 623/6 |
| 4,769,034 | 9/1988 | Poley | 623/6 |

*Primary Examiner*—Ronald Frinks
*Attorney, Agent, or Firm*—Cobrin, Feingertz & Gittes

[57] ABSTRACT

A method of implanting an intraocular lens in a human eye, includes the steps of (a) making a first incision in the eye not greater than 2.5 mm to allow a cataract lens to be extracted therefrom and a rolled intraocular lens to be inserted therethrough, the intraocular lens having a positioning hole for permitting positioning of the lens in the eye; (b) making a second incision in the eye of approximately 1 mm and spaced from the first incision to allow an intraocular lens positioning tool to be inserted therethrough; (c) pushing a rolled intraocular lens having a wrapping about at least a portion of the rolled intraocular lens into the eye through the first incision; (d) cutting the wrapping from the rolled intraocular lens in the eye so that the rolled intraocular lens unrolls in the eye; (e) removing the cut wrapping from the eye through the first incision while the lens position is maintained; and (f) final positioning of the unrolled intraocular lens in the eye.

10 Claims, 3 Drawing Sheets

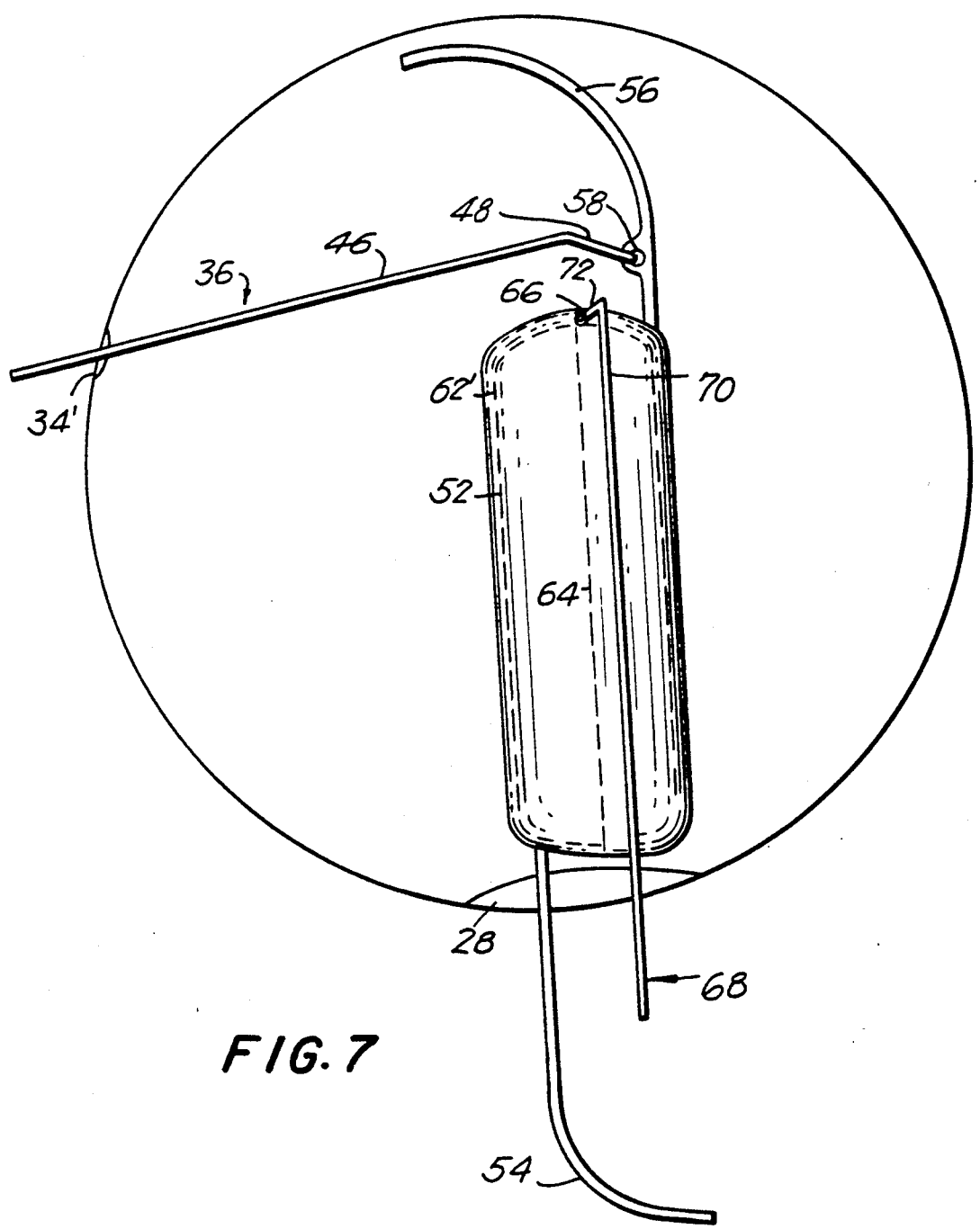

METHOD OF IMPLANTING AN INTRAOCULAR LENS IN A HUMAN EYE AND INTRAOCULAR LENS FOR SAME

BACKGROUND OF THE INVENTION

This invention relates to a method of implanting an intraocular lens in a human eye.

The natural eye in humans contains a lens which focuses images on the retina. Due to disease, naturally occurring processes or mutation, the lens may fail to function properly. For example, the lens, by mutation, may have been eliminated from the eye during its formation. Alternatively, the lens may be clouded at birth or become clouded over time. Clouding of a lens is known as a "cataract" which inhibits the transmission of visual information through the lens to the retina.

In the recent past, the removal of an impaired natural lens required a large incision into the eye at the juncture of the cornea and the sclera. As a result, healing time was substantial. Since the natural lens was removed, eyeglasses or external contact lenses were employed to help restore vision.

With the advent of intraocular lenses, incisions were still relatively large and healing time remained substantial. The length of the incision required for cataract removal initially remained substantially larger than that required for intraocular lens implantation.

Experience has shown that the longer the incision, the longer it takes to heal, the greater the danger of rupture of the incision post-operatively, and the greater the danger that poor healing will interfere with vision. Accordingly, efforts have continually been made to reduce the size of the incision. Such efforts have been successful in substantially reducing the size of the incision for cataract removal to the order of less than 8 mm, and even as small as 1.2 mm.

One proposal for reducing the length of the incision, which is the subject of U.S. Pat. No. 4,693,716 to the same inventor herein involves making the intraocular lens in multiple parts. Each part in inserted through the reduced incision and then the individual parts are assembled together in the eye. However, this technique, while permitting the use of a relatively small incision, requires special dexterity and handling by the surgeon of the multiple parts of the lens.

Another proposal for reducing the length of the incision requires the use of a very soft material for the lens, soft enough to permit the lens to be folded, inserted through the incision, and released. See, for example, U.S. Pat. No. 4,578,998. Such a lens is made in one embodiment from silicone and is extremely soft.

It is important, due to the delicate nature of certain eye structures, such as the cornea, that any intraocular lens be introduced into the eye in such a manner that it does not contact the cornea during its insertion and subsequent positioning. To accomplish this, instruments have been developed which grasp or otherwise enfold the foldable implant and accompany it through the surgical incision and into the eye, or through which the implant is injected, thus aiding in its insertion. All of these instruments, however, have the inherent disadvantage of increasing the size of the incision required for the insertion of the lens implant, since the incision must be large enough to accommodate both the implant and the instrument which grasps or enfolds the implant.

Current foldable lens implant methods require either a Bartell lens injector, or large forceps blades which fold the lens in half. These bulky, space occupying instruments increase the size of the incision required for lens insertion and may damage delicate ocular structures during and after their insertion into the eye.

Many prior art patents are devoted to techniques for improving the insertion of intraocular lenses. As an example, U.S. Pat. No. 4,439,878 discloses an intraocular lens structure for implantation in place of a cataractous natural lens. The construction features a lens element of the required prescription power and a multiple-sheet fenestrated haptic structure.

U.S. Pat. No. 4,484,515 discloses a haptic construction for an intraocular lens implant.

U.S. Pat. No. 4,249,272 discloses an intraocular lens structure. The lens features an adaptor structure assembled to an optically finished lens element having a plurality of angularly spaced stabilizing feet.

U.S. Pat. No. 4,849,271 discloses an intraocular lens structure having an adaptor structure assembled to an optically finished lens element.

U.S. Pat. No. 4,450,593 has an integral lens and haptic structure using composite laminated sheet material.

U.S. Pat. No. RE 31,968 discloses an intraocular lens having a light-focusing lens body and two position fixation means therefor.

U.S. Pat. No. 4,092,748 discloses an intraocular lens construction having a medial light-focusing lens body and two lateral position fixation elements therefor.

U.S. Pat. No. 4,174,543 discloses an intraocular lens with four-point fixation in the eyeball.

U.S. Pat. No. 4,253,200 discloses an intraocular lens with a medial light-focusing lens that includes oppositely disposed fixation means.

U.S. Pat. No. 4,840,979 discloses an intraocular lens structure which includes a first position fixation element connected to the lens which extends away from the same to the periphery of the iris for engagement in the posterior chamber.

U.S Pat. No. 4,870,760 discloses an intraocular lens which has at least a pair of position fixation elements providing multi-point support for the lens.

U.S. Pat. No. 4,268,921 discloses a multi-piece intraocular lens which includes a medial light-focusing lens body and a plurality of position fixation members for holding the lens body in proper position in the eye.

U.S. Pat. No. 4,296,501 discloses an intraocular lens which has a pair of position fixation elements providing a three-point support for the lens.

U.S. Pat. No. 4,408,454 discloses an intraocular lens having a fixation mechanism which includes a lens or optical portion having a resilient appendage attached to one end of the optical portion.

U.S. Pat. No. 4,838,687 discloses an intraocular lens having an appendage coupled to the lens portion which extends away from the lens portion to the periphery of the eye with there being a biasing means permitting movement of the appendage in relation to the lens portion.

U.S. Pat. No. 4,134,160 discloses an intraocular lens having an optical lens portion with there being an adjustable part which permits wedging of the intraocular lens beneath the optical portion of the cornea.

U.S. Pat. No. 4,159,546 discloses an intraocular lens having a plastic lens body and a plurality of flexible, memory-retaining and nonbiodegradable strands.

U.S. Pat. No. 3,991,426 discloses a posterior chamber artificial intraocular lens with a retaining means and instruments for use therewith, as does U.S. Pat. No. 4,053,953.

U.S. Pat. No. 4,056,855, U.S Pat. No. 3,711,870, U.S. Pat. No. 4,451,938, U.S. Pat. No. 4,477,931, U.S. Pat. No. 4,495,665, U.S. Pat. No. 4,585,457 and U.S. Pat. No. 4,578,998 all disclose other types of intraocular lens arrangements.

OBJECTS AND SUMMARY OF THE INVENTION

Accordingly, it is an object of the present invention to provide a method of implanting a foldable or rollable intraocular lens in a human eye.

It is another object of the present invention to provide a method of implanting a foldable intraocular lens in a human eye which minimizes the size of the incision necessary for insertion of the lens implant.

It is still another object of the present invention to provide a method of implanting an intraocular lens in a human eye in which the lens is rolled and prewrapped in a rolled configuration for insertion in the eye.

It is yet another object of the present invention to provide a method of implanting an intraocular lens in a human eye in which the lens is maintained in a rolled configuration by a wrapping therearound.

It is yet another object of the present invention to provide a method of implanting a foldable intraocular lens in a human eye in which the lens is protected by a wrapping therearound during insertion into the eye.

Still another object of the present invention is to provide a method for removal of the wrapping which surrounded the rolled or folded intraocular lens following its insertion into the eye.

In accordance with an aspect of the present invention, a method of implanting an intraocular lens in a human eye, includes the steps of (a) making a first incision in the eye of a size sufficient to allow a cataractous lens to be extracted therefrom and a folded intraocular lens to inserted therethrough; (b) pushing a rolled intraocular lens having a wrapping about at least a portion of the rolled intraocular lens into the eye through the first incision; (c) removing the wrapping from the rolled intraocular lens in the eye so that the rolled intraocular lens unfolds in the eye; and (d) positioning the unfolded intraocular lens in the eye.

In accordance with another aspect of the present invention, an intraocular lens implant for implanting an intraocular lens in a human eye, includes (a) an intraocular lens rolled about itself; and (b) a wrapping wrapped about at least a portion of the rolled intraocular lens.

The above and other objects, features and advantages of the present invention will become readily apparent from the following detailed description which is to be read in connection with the accompanying drawings.

BRIEF DESCRIPTION OF THE DRAWINGS

FIG. 7 is a front plan view of the intraocular lens and wrapping of FIG. 6 and inserted into the eye through an incision located between the cornea and the sclera; and FIG. 8 is a side elevational view of a removal tool for the lens wrapping of the present invention.

DETAILED DESCRIPTION OF THE PREFERRED EMBODIMENTS

Figure 1:
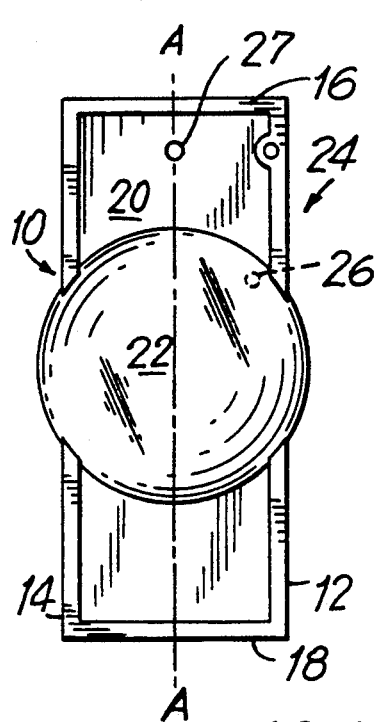
FIG. 1 is a top plan view of an intraocular lens that can be used with the present invention.

Referring to the drawings in detail, and initially to FIG. 1 thereof, a conventional intraocular lens 10 includes two longitudinally extending opposed haptics positioning member by ribs 12 and 14 and ribs 16 and 18 A web of transparent material 20 extends between the ribs, except for the central portion of the intraocular lens where an optical element 22 is located and rigidly attached to ribs 12 and 14.

The entire lens is made of a soft material capable of being easily folded, such as hydroxyethylmethyacrylate (HEMA). silicone or other acrylic material. The soft material allows the lens to be folded and is optically acceptable. Thus, a small incision on the order of 2.5 mm or less is all that is required in accordance with the present invention for inserting the intraocular lens into its position within the eye. Conventional techniques require incisions on the order of 8.5 to 4.5 mm.

Intraocular lens 10 includes a pinhole 24 which is positioned in rib 12 adjacent rib 16. Pinhole 24 is of sufficient size so that the point of a positioning tool, to be later described, can be inserted therein to hold and/or position intraocular lens 10 in the eye. Alternatively, intraocular lens 10 can have a pinhole 26 positioned in optical element 22, or a pinhole 27 can be positioned in web 20. The pinhole may be surrounded by a second, more rigid material to prevent tearing of the softer silicone or other foldable material from the force exerted by the positioning tool engaged therein.

In accordance with a first embodiment of the present invention, a first incision 28 is made in the eye at the juncture of cornea 80 and sclera 82. The size of incision 28 will be determined by two factors, the first factor being that required for cataract removal. With modern equipment, cataract removal or excision by ultrasonic destruction and suction has been developed to a point whereby the cataract can be removed by an incision of 2.5 mm or less. However, heretofore, an incision of this size was insufficient to insert the intraocular lens implant and would have to be on the order of 3.5 to 4.5 mm.

Figure 2:
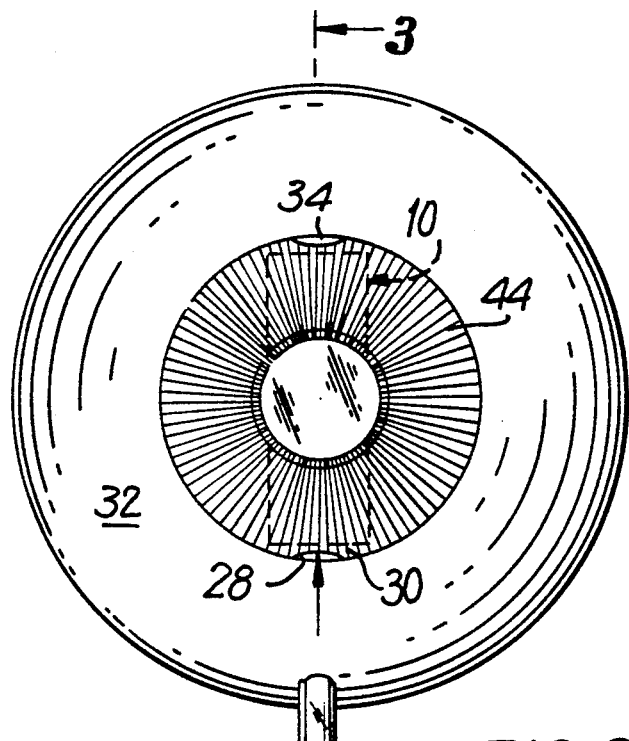
FIG. 2 is a front plan view of the intraocular lens of FIG. 1 rolled about its longitudinal axis together with a wrapping therearound and being inserted into the eye through an incision located between the cornea and the sclera.
Figure 6:
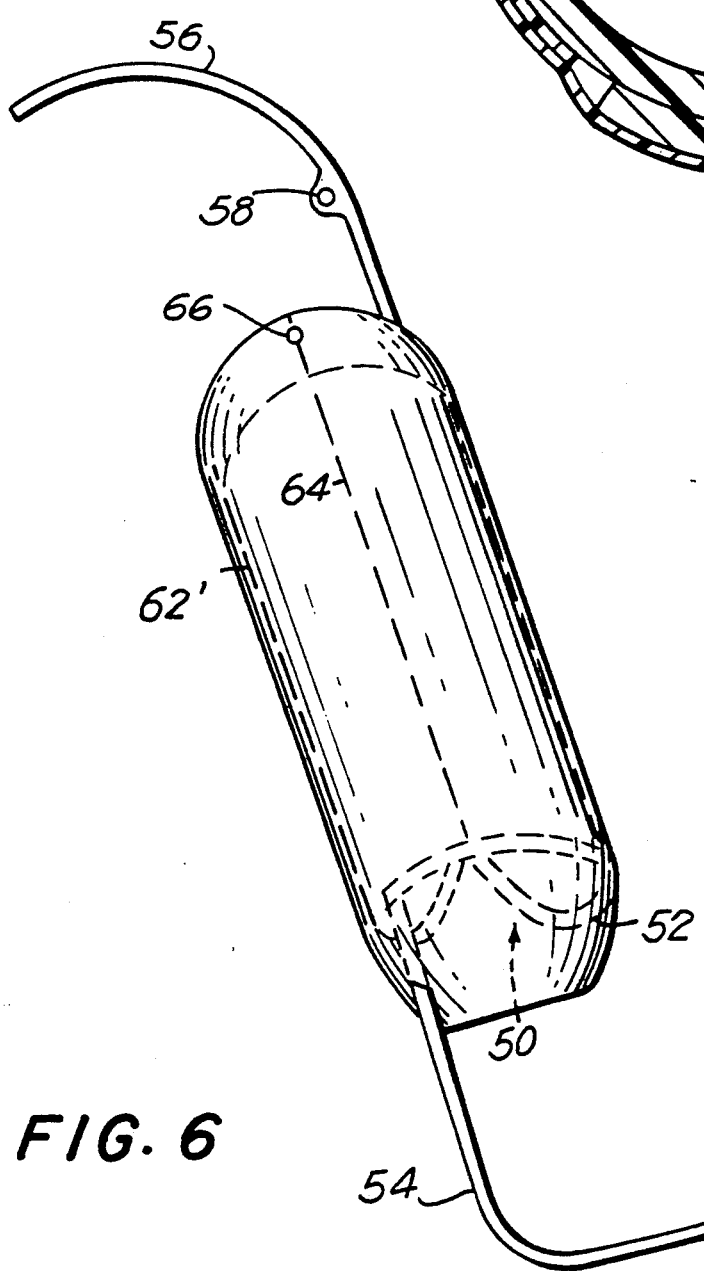
FIG. 6 is a perspective view of the lens of FIG. 4 rolled together with a wrapping for insertion in the eye.

According to the present invention, intraocular lens 10 is folded or rolled about its longitudinal axis A—A together with a wrapping 62, in much the same manner as rolling a newspaper. Thus, the rolled lens 10 and wrapping 62 can be inserted through incision 28 in the eye. Wrapping 62 is rolled with and around intraocular lens 10 to maintain intraocular lens 10 in its compact, rolled configuration, and to also protect intraocular lens 10 from damage from a tool or the like. Although wrapping 62 is shown in FIG. 2 as being wrapped about the entire length of lens 10, wrapping 62 may be pre-positioned around any part of lens 10, such as only the optical element 22 or a portion thereof, as will be apparent from the description which follows with respect to FIG. 6. Further, lens 10 and wrapping 62 can be rolled together just prior to insertion thereof into the eye, or the same may be pre-rolled and pre-packaged. Also, the ends of wrapping 62 can be in abutting or overlapping relation.

Wrapping 62 may be made of any suitable material, such as plastic, polypropylene, silicone, polyvinyl chloride, TEFLON (polytetrafluoroethylene), "Cellophane" or any other suitable pliable material, and preferably has a thickness in the range of 0.01 mm to 0.1 mm. In such case, rolled lens 10, together with wrapping 62, can be inserted through the 2.5 mm incision 28 in the eye. It will be appreciated that the thickness of wrapping 62 is sufficiently small so as not to hinder the insertion of lens 10 and wrapping 62 through incision 28.

Wrapping 62 may encase the rolled lens 10 and the tip of an instrument (not shown), such as a forceps, to be used for lens positioning or manipulation before or after unwrapping lens 10 in the eye.

Prior to insertion of folded intraocular lens 10 and wrapping 62 through incision 28, a second puncture 34 is made in the eye at the juncture of the cornea and the sclera, opposite first incision 28. Puncture 34 is of the order of 1 mm or less, as such incision will accommodate the lateral dimension of a positioning tool which is inserted through puncture 84. The use of a puncture as described herein is standard operating procedure in cataract surgery and does not require a suture. One such positioning tool 36 is shown in FIG. 8 and includes an arm 38 having a pointed straight-hooked tip 40. The size of puncture 34 is sufficient to allow tip 40 and part of arm 88 to be inserted therethrough and 1 mm will usually suffice.

Accordingly, wrapping 62 and lens 10 can be inserted into the eye through incision 28 by a conventional tool.

Specifically, following cataract extraction through incision 28 by conventional means, intraocular lens 10 is folded about its longitudinal axis A—A, together with wrapping 62 therearound, such that pinhole 24 or 26 is exposed. A conventional forceps is used to insert the folded intraocular lens 10 and wrapping 62 into incision 28. It is important to note that the forceps is not inserted into the eye, thereby eliminating the need for a larger incision to accommodate this instrument and the potential for damaging intraocular structure with the instrument itself. Following lens insertion, positioning tool 36 is extended through puncture 84, and tip 40 grips pinhole 24 so that the folded intraocular lens 10 and wrapping 62 is held in its position while instrument 68 is used to remove the wrapping 62. Because intraocular lens 10 is folded about its longitudinal axis, incision 28 is relatively small, on the order of 2.5 mm or less.

Accordingly, lens 10 spontaneously unfolds, being kept away from contact with the cornea by a slight rearward (posterior) pressure by the surgeon upon the lens with the positioning tool so as to assume the position shown in FIG. 8.

After intraocular lens 10 is positioned as desired, which in most cases will be in the posterior chamber of the eye behind the iris 44, like the natural lens it replaces, the positioning tool 36 is removed through puncture 34. The net result is the implantation of the intraocular lens 10 in the posterior chamber of the eye with incisions on the order of 2.5 mm or less, which is less than those heretofore made.

Figure 4:
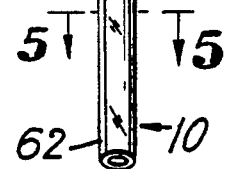
FIG. 4 is a top plan view of an alternative form of an intraocular lens with haptics that can be used with the present invention.
Figure 4:
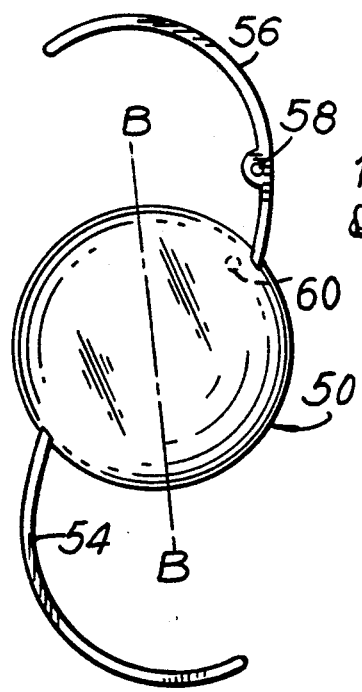
Figure 3:
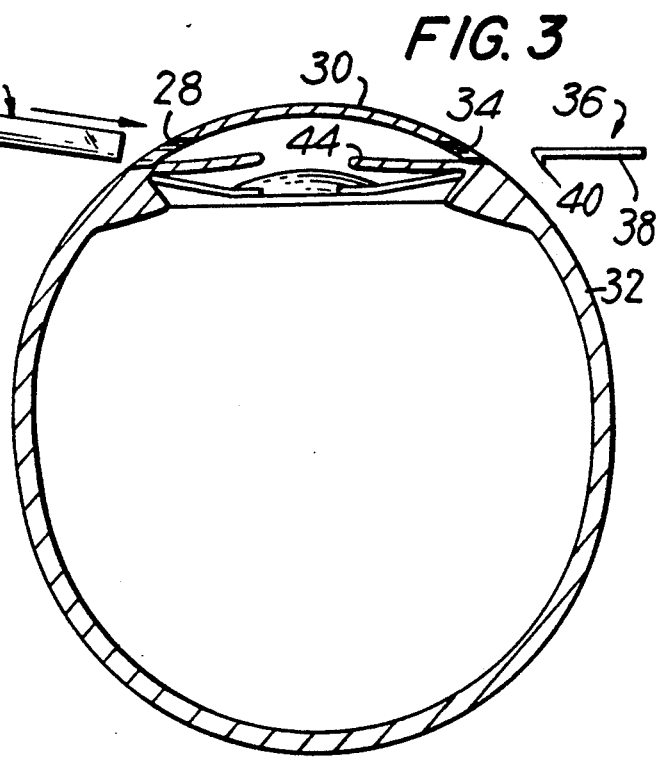
FIG. 3 is a cross-sectional view taken substantially along line 3—8 of FIG. 2.
Figure 5:
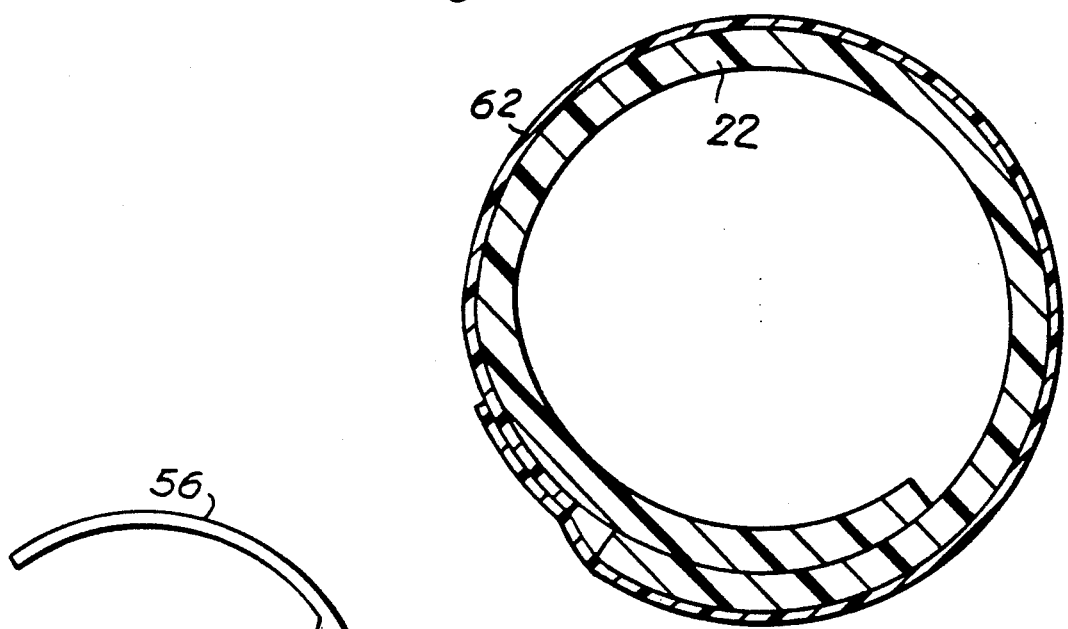
FIG. 5 is a cross-sectional view of the rolled lens and wrapping of FIG. 2, taken along line 5—5 thereof.

In FIG. 4, an intraocular lens 50, which differs in design from intraocular lens 10 is shown. Intraocular lens 50 includes an optical element 52 made of silicone or other soft foldable lens material, having haptics positioning member 54 and 56 made of a non-soft standard material, such as PMMA or PROLENE (polypropylene). Positioning hole 58 can be formed at haptic 56 or, alternatively, at optical element 52, as shown in phantom lines by reference numeral 60. The positioning hole can be surrounded by a second, more rigid material, such as PMMA or other material, as described above.

In accordance with the present invention, intraocular lens 50 is folded about its longitudinal axis B—B, together with a wrapping 62' such that pinhole 58 is on the exterior thereof. The insertion of intraocular lens 50 and wrapping 62' into the eye then follows the steps heretofore described in conjunction with intraocular lens 10.

Removal of wrappings 62 and 62' may be accomplished in many different ways in accordance with the present invention.

For example, wrapping 62 or 62' can be removed by mechanical means. In such case, a forceps can be used to peel or tear wrapping 62 or 62' during, or preferably after, lens insertion into the eye. As a specific example of such mechanical means, reference will be made to FIGS. 6 and 7, where wrapping 62' is formed with a longitudinal perforation 64 extending along the entire length thereof. In addition, the upper end of wrapping 62' contains a hole 66 in alignment with perforation 64, the purpose of which will be apparent from the discussion which follows.

As shown in FIGS. 7 and 8, a small microsurgical instrument 68 can be used to tear wrapping 62'. Instrument 68 includes an elongated shaft 70, having an arcuate blade 72 with a sharp cutting edge, blade 72 extending substantially perpendicular from shaft 70. A hook 74 is secured to the opposite end of blade 72 and extends rearwardly toward shaft 70 and is set at a slight angle inwardly toward shaft 70. Hook 74 is provided to grasp wrapping 62' and to also shield lens 50 from blade 72.

Specifically, instrument 68 is inserted through incision 28 in the eye, hook end first. Hook 74 is then engaged in hole 66 in wrapping 62'. As instrument 68 is removed from the eye through incision 28, blade 72 thereof tears wrapping 62' along perforation 64. Accordingly, lens 50 is no longer restrained by wrapping 62', and spontaneously unfolds within the eye. The cut wrapping 62' is then removed from the eye by a hooked instrument, such as the hook end of instrument 68, or by a standard forceps, through the same incision 28. Because of the relatively thin and deformable nature of wrapping 62', it can easily be removed through incision 28.

In order to prevent movement of lens 50 and wrapping 62' within the eye during removal of instrument 68, microsurgical positioning tool 86 is inserted through a second puncture 34' in the eye at the juncture of the cornea and the sclera. The use of a puncture as described herein is standard operating procedure in cataract surgery and does not require a suture. Puncture 34' is of the order of 1 mm or less, as such incision will accommodate the lateral dimension of the positioning tool 36 which is inserted through puncture 34'. The size of puncture 34' is sufficient to allow tip 48 and part of arm 46 to be inserted therethrough, and accordingly, 1 mm will usually suffice. Tip 48 engages in hole 58 in haptic 56 of lens 50 that is in the eye. The wrapping is removed by tool 68 by tearing the wrapping along perforation 64 while the lens is held stationary such that the removal of the wrapping allows the lens to unfold and not move in any other way. Alternatively, instead of providing perforation 64, a sharp knife can be used to start an incision in wrapping 62 or 62′. In such case, a hard firm rod or plate can be inserted along the length and inside of wrapping 62 or 62′ to serve as a cutting board so that lens 10 or 50, respectively, is not damaged by the knife used to cut wrapping 62 or 62′.

Wrappings 62 and 62′ may also be removed from the lens and the eye by chemical means. For example, bonding of wrapping 62 or 62′ to itself and/or to the lens, can be chemically dissolved. In such case, a dissociative chemisorption process, well known to chemists, could be used.

It is contemplated that standard lenses will be used in the present invention, e.g., those having 6.0 or 7.0 mm diameters.

It is also within the contemplation of the present invention that the wrapping may be scored rather than perforated. However, either technique may be used as desired.

Having described specific preferred embodiments of the invention with reference to the accompanying drawings, it will be appreciated that the present invention is not limited to those precise embodiments, and that various changes and modifications may be effected therein by one of ordinary skill in the art without departing from the scope or spirit of the invention as defined in the appended claims.

What is claimed is:

1. A method of implanting an intraocular lens in a human eye, comprising the steps of:
   (a) making a first incision in the eye of a size sufficient to allow a cataractous lens to be extracted therefrom and a rolled intraocular lens to be inserted therethrough;
   (b) pushing a rolled intraocular lens having a pliable wrapping about at least a portion of the rolled intraocular lens into the eye through said first incision;
   (c) removing said wrapping from said rolled intraocular lens in the eye so that said rolled intraocular lens unrolls in the eye;
   (d) positioning said unrolled intraocular lens in the eye;
   (e) rolling said intraocular lens together with said wrapping so that said wrapping surrounds at least a portion of the rolled intraocular lens.

2. A method according to claim 1 wherein said step of making a first incision includes the step of making said first incision with a length not greater than 2.5 mm at the juncture of the cornea and sclera in the eye.

3. A method of implanting an intraocular lens in a human eye, comprising the steps of:
   (a) making a first incision in the eye of a size sufficient to allow a cataractous lens to be extracted therefrom and a rolled intraocular lens to be inserted therethrough;
   (b) pushing a rolled intraocular lens having a wrapping about at least a portion of the rolled intraocular lens into the eye through said first incision, said wrapping being formed with a longitudinal perforation;
   (c) removing said wrapping from said rolled intraocular lens in the eye so that said rolled intraocular lens unrolls in the eye;
   (d) positioning said unrolled intraocular lens in the eye;
   (e) inserting an instrument having a blade into the eye through said first incision;
   (f) cutting said wrapping with said blade along the perforation line thereof of free said intraocular lens from said wrapping, wherein said lens unrolls in said eye; and
   (g) removing said cut wrapping from said eye through said first incision.

4. A method according to claim 3 wherein said wrapping includes a hole at an edge thereof in alignment with said perforation line, and said instrument has a hook end connected with said blade, and said step of cutting includes the steps of inserting said hook end into said hole and removing said instrument so that said blade cuts said wrapping along said perforation line.

5. A method of implanting an intraocular lens in a human eye, comprising the steps of:
   (a) making a first incision in the eye of a size sufficient to allow a cataractous lens to be extracted therefrom and a rolled intraocular lens to be inserted therethrough;
   (b) pushing a rolled intraocular lens having a pliable wrapping about at least a portion of the rolled intraocular lens in the eye through said first incision;
   (c) removing said wrapping from said rolled intraocular lens in the eye so that said rolled intraocular lens unrolls in the eye;
   (d) positioning said unrolled intraocular lens in the eye; and
   (e) said wrapping is bonded to itself or to said lens, and said step of removing includes the step of chemically dissolving said bond.

6. A method according to claim 5; wherein said step of chemically dissolving includes the step of dissolving by dissociative chemisorption.

7. An intraocular lens for implantation in a human eye, comprising:
   (a) an intraocular lens rolled about itself; and
   (b) a wrapping wrapped about at least a portion of said rolled intraocular lens, said wrapping being bonded to itself.

8. An intraocular lens for implantation in a human eye, comprising:
   (a) an intraocular lens rolled about itself; and
   (b) a wrapping wrapped about at least a portion of said rolled intraocular lens, said wrapping being bonded to said lens.

9. An intraocular lens for implantation in a human eye, comprising:
   (a) an intraocular lens rolled about itself; and
   (b) a wrapping wrapped about at least a portion of said rolled intraocular lens, said wrapping including a perforation extending longitudinally therealong.

10. An intraocular lens implant according to claim 9, wherein said wrapping includes a hole for receiving a hook, said hole being in alignment with said perforation.

* * * * *